United States Patent [19]

Drake et al.

[11] Patent Number: 4,517,006

[45] Date of Patent: May 14, 1985

[54] COMPOSITE MATERIALS COMPRISING WATER-SOLUBLE GLASS PARTICLES

[75] Inventors: Cyril F. Drake, Harlow; Ronald Jones, Sawbridgeworth, both of England

[73] Assignee: ITT Industries, Inc., New York, N.Y.

[21] Appl. No.: 442,376

[22] Filed: Nov. 17, 1982

[30] Foreign Application Priority Data

Nov. 18, 1981 [GB] United Kingdom ............... 8134752

[51] Int. Cl.$^3$ ...................... A01N 25/26; A61K 9/26; A61K 9/52; C05B 17/00
[52] U.S. Cl. ...................... 71/64.11; 71/65; 71/67; 71/79; 71/DIG. 1; 71/904; 424/19; 424/22; 424/23; 424/26; 424/27; 424/28; 424/29; 424/30; 428/229; 428/241; 428/283; 428/305.5; 428/317.9; 428/372; 428/406; 428/913; 501/45; 501/47; 501/48; 523/122; 523/124; 601/890
[58] Field of Search ............... 71/64.11, 904; 424/19, 424/22, 23, 26, 27, 28, 29, 30; 428/229, 241, 283, 305.5, 317.9, 372, 406, 913; 501/45, 47, 48; 523/122, 124; 604/890

[56] References Cited

U.S. PATENT DOCUMENTS

| 3,959,556 | 5/1976 | Morrison | 428/364 |
| 4,111,922 | 9/1978 | Beede et al. | 428/289 |
| 4,123,248 | 10/1978 | Drake | 501/45 |
| 4,343,853 | 8/1982 | Morrison | 428/293 |
| 4,349,025 | 9/1982 | Drake | 424/22 |
| 4,401,712 | 8/1983 | Morrison | 428/289 |
| 4,473,545 | 9/1984 | Drake et al. | 424/22 |

Primary Examiner—James C. Cannon
Attorney, Agent, or Firm—James B. Raden

[57] ABSTRACT

A composite material for the controlled release of an active substrate comprises a relatively insoluble, e.g. polymeric, matrix (11) in which a soluble particulate material (12) is dispersed. When the composite is placed in an aqueous medium dissolution of the particulate material substantially increases the water permeability of the matrix. This effect may be used to provide for the controlled release of an active material into the aqueous medium.

10 Claims, 2 Drawing Figures

COMPOSITE MATERIALS COMPRISING WATER-SOLUBLE GLASS PARTICLES

This invention relates to arrangements and methods for the controlled release of active materials into solution.

There is a broad range of applications wherein it is necessary to provide for the release of an active material at a controlled rate into an aqueous environment. In the biosciences, particularly, the potential for prolonging the action of numerous bioactive compounds is stimulating considerable interest.

Since the early 1950's researchers have attempted to develop controlled release compounds able to store active materials and then release them at controlled rates into aqueous systems. This research has tended to concentrate on polymeric materials. Any polymers may be fabricated at relatively low temperatures to encapsulate effectively active materials thereby protecting them from unwanted interaction with the environment. Subsequent release of the active material is effected by one of four general mechanisms, i.e. diffusion, swelling, (bio) chemical action and magnetic processes. However, in most cases it has proved impractical to engineer the required degree of control, especially over long periods, and in many instances toxicity of the special polymer itself has limited exploitation.

Controlled Release Glasses (CRG), such as those described in U.S. Pat. No. 4,350,675, are inorganic glasses that may be formulated to be non-toxic. Their solution rates in aqueous media are chemically controlled and may be varied to give a high degree of precision, even over long periods. Unfortunately CRG may only be fabricated at temperatures that would, on contact, destroy or degrade many of the active materials of interest. For this reason the development of CRG has tended to be concentrated on applications requiring the release of inorganic materials.

The object of this invention is to combine the most advantageous properties of both the polymer and CRG approaches, without risk of toxicity. Thus the benefits of low temperature fabrication and release control combine to provide a new means of releasing a wide range of active materials.

According to the invention there is provided a coherent composite structure, comprising a composite material and an active material, said composite material comprising a matrix material and a particulate material soluble in an aqueous medium and dispersed in said matrix material, the composite material being such that, when contacted with the aqueous medium, said particulate material dissolves thereby increasing the aqueous permeability of said composite whereby in use to control the release of the active material from the structure.

Typically the matrix material is a polymer.

When the composite comes into contact with an aqueous medium the particulate material dissolves to provide a series of passageways through the host matrix thus permitting the ingress of water. Such a composite can be employed for the delayed and controlled release of an active material which, prior to the dissolution of the particulate material and the consequent significant increase in the water permeability of the composite, is protected by the composite itself.

Advantageously the particulate material is a soluble glass composition or a mixture of such glass compositions. Water soluble glass compositions have the important property that their dissolution rate may be tailored to a desired value by composition adjustment thus providing for the manufacture of composite materials with a wide range of release characteristics. Moreover, many of these glasses are biologically inert.

Embodiments of the invention will now be described with reference to the accompanying drawings in which.

Figure 1:
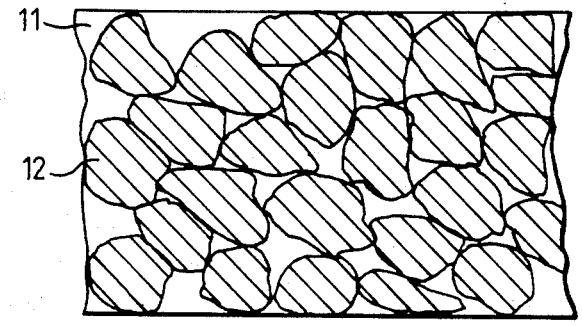
FIG. 1 is a cross section of a portion of a composite structure.
Figure 2:
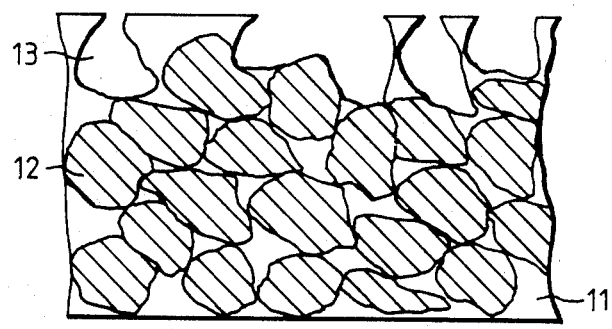
FIG. 2 illustrates the effect of an aqueous medium on the composite structure shown in FIG. 1.

Referring to the drawings, the composite shown comprises a host matrix 11, of a relatively low solubility or of essentially insoluble material, e.g. a polymer, in which matrix a soluble particulate material 12 is dispersed. The loading of the particulate material 12 in the polymer 11 is sufficient to ensure that each particle 12 is in contact with at least two similar particles. When the structure is placed in water or an aqueous medium the particulate material 12 dissolves to provide an array of passageways 13 (FIG. 2) through the polymeric matrix thus significantly increasing the water permeability of the composite.

The composite may be employed to provide for the controlled release of an active material that is either dispersed within it or is coated with it or covered by it.

The polymeric matrix 11 may comprise a wide variety of materials. For biological and medical applications we prefer to employ cellulosic materials, but other materials may of course also be employed. Typical of such polymers, though by no means limiting, are polyene, polyesters, polyamides, polysaccharides, natural gums and latexes, and mixtures and copolymers thereof. Advantageously, in some applications, the polymer matrix may be thermosetting or thermoplastic thus permitting low cost bulk fabrication by any of the known techniques, e.g. pressing or extruding. Equally the polymer may be cross-linked by any of the known techniques.

The particulate material is preferably a substance having a controllable dissolution rate in an aqueous medium, i.e. the material is of such a nature that, by suitable adjustment of its composition, a predeterminable dissolution rate can be obtained. The best known examples of such materials are the controlled release glasses. These are water soluble glass compositions whose dissolution rate in an aqueous medium is determined by the relative proportions of the various glass forming and glass modifying constituents.

We prefer to employ phosphate or borate glasses for this purpose as such materials are relatively non-toxic and also simple to prepare. Furthermore, the techniques for controlling the dissolution rate of these glass systems are well understood. The glasses generally comprise phosphorous pentoxide, boric oxide or mixtures thereof, as the glass forming oxide of the glass together with one or more further oxides which provide the glass modifying constituents of the composition. The dissolution rate, and the pH of solutions of such compositions are determined by the nature and proportion of the glass modifying oxide or oxides and by the overall molar ratio of glass modifier to glass former.

We have also found that the presence of certain metal oxides, for example the oxides of most two or three valent metals, reduces the dissolution rate of a glass composition whilst the presence of other metal oxides, in particular alkali metal oxides, increases the dissolution rate. Thus, by suitable adjustment of the ratio of glass-formers to glass modifiers and proportions of these two types of oxides a wide range of dissolution rates can be obtained. The techniques of glass dissolution rate and solution pH control are more fully described in U.S. Pat. No. 4,350,675. Typical of suitable glass compositions, but by no means limiting, are alkali metal/phosphate glasses and alkali metal/borate glasses.

The composite material may be manufactured by a number of techniques according to the ultimate application of the material. Thus the particulate material may be mixed with the solid or liquid polymer and cast, pressed or moulded to form monolithic blocks or the two may be extruded together into rods, tubes, or fibres. The particulate material may also be incorporated in a flim of the polymer to form either a self supporting layer or a surface coating to be applied to a solid body. Other techniques include spray granulations of mixtures of the particulate material with the polymers.

In all these processes, except those in which the composite is in the form of a film, the volume proportion and/or form of distribution of the particulate material in the composite structure should be sufficient to ensure that each particle is in contact with at least two similar particles. Typically this requires a volume proportion of at least 50% of the total volume and preferably at least 67%. In some applications the composite may contain as much as 90 volume % of the particulate material, this high concentration being achieved by the incorporation of a mixture of large and small particles into the polymer.

In the case of the film-type composite it may only be necessary that there should be a plurality of parallel paths through the thickness of the film, each path consisting of a single particle or a chain of contacting particles.

The body of materials described herein may be used in a variety of applications as structures whereby an active material is stored and then subsequently released into an aqueous medium at a controlled and predetermined rate. In many applications it may be desirable to minimise the water permeability of the composite prior to dissolution of the glass. This requires that the glass be wetted by the polymer. Since the glasses described herein are typically hydrophilic we prefer, in such applications, to select polymers that are not non-polar.

Where the body is in the form of a monolithic block or granules containing one or more active materials either homogeneously or heterogeneously dispersed throughout it and is subsequently immersed in an aqueous medium, the particulate material dissolves thus providing passageways through the polymer. This significantly increases the water permeability of the composite and allows the active material to dissolve out. Such an arrangement is suitable for bulk distribution of an active material which material may comprise e.g. a fertiliser, a selective or non-selective herbicide, an insecticide, a pheromone, a moluscicide, a nematicide, a fungicide, an algicide, a slimicide, a rodenticide, or mixtures thereof. The applications of such a structure include, but are not limited to, soil and crop treatment, biocidal purification of water courses, corrosion protection and the inhibition of bacterial growth in water systems. In a further application a medicament or drug may be incorporated in the structure which may be administered to a human or animal patient either internally, in the form of a tablet, implant or suppository (or a bolus for ruminant animals), or externally as a percutaneous device. The medicament or drug may comprise a nutrient, a prophylactic agent, a therapeutic agent, an antibiotic, an antiseptic agent, a parasiticide, a hormone or contraceptive.

The monolithic body may be formed into a single or multi-cavity structure the cavities of which contain a liquid or solid drug or medicament. A single cavity structure of this kind, when contacted by an aqueous medium, provides a controlled delay prior to release of the active content. Where a multicavity device is employed, a predetermined or programmed release rate profile may be obtained.

It is often advantageous to employ a polymeric material that has an appreciable but very low dissolution rate or that is biodegradable. This ensures that ultimately no solid residue is left.

Moreover, in the case where the active material is dispersed within the polymeric matrix the release rate profile is determined by the relative rate of dissolution of the particulate material to the dissolution, degradation, or erosion rate of the polymer. It can be shown that if the former dissolution rate is significantly greater than the latter then the rate of transfer of the active material to solution follows approximately a square root law, whereas if the two rates are similar then the rate of transfer approximates to a linear law.

In a particularly advantageous arrangement the active material is granular and is formed into a body wherein the granules are cemented together by a composite comprising a polymer and a powdered water soluble glass. The glass particles are significantly smaller than the active material granules so that the composite acts as a 'mortar' between the granules thus providing a coherent body. The body may be formed e.g. by pressing, extrusion or casting.

In a further embodiment the composite structure may be produced as a film either by film casting techniques or by pressing. The film may be self supporting or it may be employed in the form of a surface coating on a solid substrate.

The film may be employed as an encapsulent which is applied, e.g. by heat shrinking, to a body containing an active material. When such an encapsulated body is placed in an aqueous medium the encapsulent coating protects the body from dissolution for a predetermined period or until particular conditions, i.e. a desired solution pH, are satisfied.

The encapsulated body may comprise a pill or tablet for oral administration to a human or animal patient, the coating providing a predetermined delay prior to release of the active substances contained in the pill or tablet. In a particularly advantageous arrangement a plurality of such devices, each with a different dissolution rate or different thickness coating, are sealed in a single soluble, e.g. gelatin, casing. When this device is administered to a patient the casing dissolves releasing the individual capsules each of which then releases its active content after a different predetermined delay. This provides the patient with regular doses of the active material over a period of several hours or days.

In a further embodiment the active material is in granular form and the individual granules are each coated with the film to produce a granular product in which, after coming into contact with an aqueous medium, there is a delay before the active material starts to dissolve in the aqueous medium.

The composite material may be applied as a surface coating on a solid substrate from a slurry of the particulate material in a thermosetting polymer. The slurry is applied to the surface by brushing, spreading or spraying and is then cured to a coherent material by heating, chemical cross-linking, physical cross linking, solvent evaporation, or by applying energy in the form of light or other electromagnetic radiation. In such an arrangement an active material is incorporated in the composite, the active material being released when dissolution of the particle material allows water to diffuse into the composite. The active material for such applications may be an anti-foulant, e.g. for marine use, a corrosion inhibiting agent or an antiseptic material.

We claim:

1. A coherent composite structure releasably incorporating an active material therein, said composite structure comprising a polymeric matrix material and a particulate glass composition dispersed in said matrix material, said polymeric matrix material being essentially insoluble in aqueous medium and said particulate glass composition being soluble at a controlled dissolution rate in said aqueous medium whereby said composite structure shields said active material from release until contacted by said aqueous medium and when said composite structure is contacted by said aqueous medium, said particulate glass composition dissolves at a controlled rate thereby increasing the aqueous permeability of said composite structure to release said active material incorporated therein at a controlled rate, said particulate glass composition consisting essentially of from 50–75 mole percent of phosphorus pentoxide as a glass forming oxide; from 1–20 mole percent of an alkali metal oxide as the principal glass modifier, the remainder including from 1–25 mole percent of an oxide selected from the group consisting of an alkaline earth metal oxide, an oxide of a metal of Group III A of the Periodic Table, a transition metal oxide and combinations of the foregoing.

2. The composite structure of claim 1, wherein a portion, not exceeding 10 mole percent of the phosphorus pentoxide in said particulate glass composition is replaced by another glass-forming oxide selected from the group consisting of $SiO_3$, $B_2O_3$, $GeO_2$, $As_2O_3$ and $Sb_2O_3$.

3. A structure as claimed in claim 1 and in the form of a monolithic block woven or single fibres, a sheet, a film or granules.

4. A structure as claimed in claim 1, wherein the active material selected from the group consisting of fertilisers, selective or non-selective herbicides, insecticides, pheromones, molluscides, larvicides, nematocides, fungicides, algicides, slimicides, rodenticides, or mixtures thereof.

5. A structure as claimed in claim 1, wherein the active material is selected from the group consisting of nutrients, prophylactic agents, therapeutic agents, antibiotics, antiseptic agents, parasiticides, hormones, and contraceptives.

6. A structure as claimed in claim 1, wherein the particulate glass material comprises 50–90% by volume of the composite material.

7. A therapeutic device being an implant or percutaneous device, a bolus or other device capable of oral, rectal or surgical administration formed from a structure as claimed in claim 1.

8. A device as claimed in claim 7, wherein the composite is in the form of a film or sheet comprising a surface coating on a solid body.

9. A device as claimed in claim 7, wherein the structure is in the form of a body containing one or more cavities each containing active material.

10. A device as claimed in claim 9, wherein the active material is a drug or medicament.

* * * * *